(12) United States Patent
Tierney et al.

(10) Patent No.: US 8,502,199 B2
(45) Date of Patent: Aug. 6, 2013

(54) BLUE-SHIFTED TRIARYLAMINE POLYMER

(75) Inventors: Brian Tierney, Cambridgeshire (GB);
Mark Leadbeater, Depden (GB);
Nalinkumar Patel, Cambridge (GB);
Clare L. Foden, Cambridge (GB);
Natasha M. Conway, Cambridge (GB);
Mary J. McKiernan, Cambridgeshire (GB)

(73) Assignees: Cambridge Display Technology Limited, Cambridgeshire (GB); CDT Oxford Limited, Cambridgeshire (GB)

( * ) Notice: Subject to any disclaimer, the term of this patent is extended or adjusted under 35 U.S.C. 154(b) by 571 days.

(21) Appl. No.: 11/813,180

(22) PCT Filed: Dec. 23, 2005

(86) PCT No.: PCT/GB2005/005056
§ 371 (c)(1),
(2), (4) Date: Oct. 9, 2008

(87) PCT Pub. No.: WO2006/070184
PCT Pub. Date: Jul. 6, 2006

(65) Prior Publication Data
US 2009/0146164 A1    Jun. 11, 2009

(30) Foreign Application Priority Data

Dec. 29, 2004  (GB) .................................. 0428445.1

(51) Int. Cl.
| | | |
|---|---|---|
| C07C 211/56 | (2006.01) |
| H01L 33/00 | (2010.01) |
| C08G 61/12 | (2006.01) |
| C08G 73/02 | (2006.01) |
| C08L 65/00 | (2006.01) |
| C09K 11/06 | (2006.01) |
| H01L 21/00 | (2006.01) |
| H01L 51/00 | (2006.01) |
| H05B 33/14 | (2006.01) |

(52) U.S. Cl.
USPC ............. 257/40; 428/917; 313/504; 313/506; 252/301.16; 252/301.35; 57/E51.001; 438/29; 438/99; 528/422; 528/397; 528/394

(58) Field of Classification Search
USPC ............ 528/422, 397, 394; 257/40, E51.001; 438/29, 99; 428/411.1
See application file for complete search history.

(56) References Cited

U.S. PATENT DOCUMENTS

| | | | |
|---|---|---|---|
| 5,523,555 A | 6/1996 | Friend et al. |
| 5,621,131 A | 4/1997 | Kreuder et al. |

(Continued)

FOREIGN PATENT DOCUMENTS

| | | |
|---|---|---|
| EP | 0 707 020 | 4/1996 |
| EP | 0 842 208 | 5/1998 |

(Continued)

OTHER PUBLICATIONS

Marsitzky et al (Self-encapsulation of Poly-2,7-fluorenes in a dendrimer matrix, Journal of the American Chemical Society, vol. 123, No. 29, 2001, pp. 6965-6972).*

(Continued)

*Primary Examiner* — Randy Gulakowski
*Assistant Examiner* — Rachel Kahn
(74) *Attorney, Agent, or Firm* — Marshall, Gerstein & Borun LLP

(57) ABSTRACT

A semiconductive conjugated polymer comprising a first repeat unit comprising general formula I:

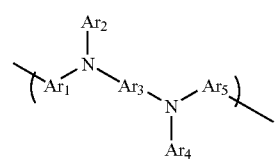

where $Ar_1$, $Ar_3$, and $Ar_5$ are the same or different and wherein each represents an optionally substituted aryl or heteroaryl group; $Ar_2$ and $Ar_4$ are the same or different and each represent a substituted aryl or heteroaryl group; and $Ar_2$ and $Ar_4$ sterically interact with one another so as to cause an increase in the bandgap of the polymer.

23 Claims, 5 Drawing Sheets

U.S. PATENT DOCUMENTS

| | | | |
|---|---|---|---|
| 5,723,873 | A | 3/1998 | Yang |
| 5,728,801 | A | 3/1998 | Wu et al. |
| 5,798,170 | A | 8/1998 | Zhang et al. |
| 6,268,695 | B1 | 7/2001 | Affinito |
| 6,353,083 | B1 | 3/2002 | Inbasekaran et al. |
| 6,830,832 | B2 * | 12/2004 | Oguma et al. ............... 428/690 |
| 6,861,502 | B1 * | 3/2005 | Towns et al. ............... 528/422 |
| 6,953,638 | B2 | 10/2005 | Kamatani et al. |
| 7,030,138 | B2 | 4/2006 | Fujimoto et al. |
| 7,094,477 | B2 | 8/2006 | Kamatani et al. |
| 7,125,998 | B2 | 10/2006 | Stossel et al. |
| 7,147,935 | B2 | 12/2006 | Kamatani et al. |
| 7,238,435 | B2 | 7/2007 | Kamatani et al. |
| 7,586,006 | B2 | 9/2009 | Funahashi |
| 2001/0037012 | A1 | 11/2001 | Towns et al. |
| 2002/0117662 | A1 | 8/2002 | Nii |
| 2002/0182441 | A1 | 12/2002 | Lamansky et al. |
| 2004/0054232 | A1 | 3/2004 | Hosokawa et al. |
| 2004/0077824 | A1 | 4/2004 | O'Dell et al. |
| 2006/0058494 | A1 | 3/2006 | Busing et al. |
| 2006/0149022 | A1 | 7/2006 | Parham et al. |

FOREIGN PATENT DOCUMENTS

| | | |
|---|---|---|
| EP | 0 880 303 | 11/1998 |
| EP | 0 901 176 A2 | 3/1999 |
| EP | 0 947 123 | 10/1999 |
| EP | 0 949 850 | 10/1999 |
| EP | 1 219 590 | 7/2002 |
| EP | 1 245 659 A1 | 10/2002 |
| EP | 1 289 015 | 3/2003 |
| GB | 2 348 316 | 9/2000 |
| JP | 2002-324679 | 11/2002 |
| WO | WO-90/13148 A1 | 11/1990 |
| WO | WO-96/16449 A1 | 5/1996 |
| WO | WO-98/57381 | 12/1998 |
| WO | WO-99/48160 | 9/1999 |
| WO | WO-99/54385 | 10/1999 |
| WO | WO-00/48258 | 8/2000 |
| WO | WO-00/53656 A1 | 9/2000 |
| WO | WO-00/55927 A1 | 9/2000 |
| WO | WO 01/19142 | 3/2001 |
| WO | WO-01/62869 | 8/2001 |
| WO | WO 0168740 A1 * | 9/2001 |
| WO | WO-03/035714 | 10/2001 |
| WO | WO-01/81649 | 11/2001 |
| WO | WO-02/31896 | 4/2002 |
| WO | WO-02/44189 | 6/2002 |
| WO | WO-02/45466 | 6/2002 |
| WO | WO-02/066552 | 8/2002 |
| WO | WO-02/068435 | 9/2002 |
| WO | WO-02/081448 | 10/2002 |
| WO | WO-02/084759 | 10/2002 |
| WO | WO-02/092723 | 11/2002 |
| WO | WO-02/092724 | 11/2002 |
| WO | WO-03/018653 | 3/2003 |
| WO | WO-03/022908 | 3/2003 |
| WO | WO-03/095586 | 11/2003 |
| WO | WO-2004/037887 | 5/2004 |
| WO | WO-2004/070772 | 8/2004 |
| WO | WO-2004/084260 | 9/2004 |
| WO | WO 2004/092111 | 10/2004 |

OTHER PUBLICATIONS

Bernius et al., "Progress with Light-Emitting Polymers," *Adv. Mater.*, 2(23):1737-1750 (2000).

Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).

Setayesh et al., "Bridging the Gap Between Polyfluorene and Ladder-Poly-p-phenylene: Synthesis and Characterization of Poly-2,8-indenofluorene," *Macromolecules*, 33:2016-2020 (2000).

Yamaguchi et al., "Effects of B and C on the Ordering of $L1_{0-CoPt}$ Thin Films," *Appl. Phys. Lett.*, 79(13):2001-2003 (2001).

Yamamoto, "Electrically Conducting and Thermally Stable π-Conjugated Poly(arylene)s Prepared by Organometallic Processes," *Prog. Polym. Sci.*, 17:1153-1205 (1993).

Yang et al., "Efficient Blue Polymer Light-Emitting Diodes from a Series of Soluble Poly(paraphenylene)s," *J. Appl. Phys.*, 79(2):934-939 (1996).

International Preliminary Report on Patentability for International Application No. PCT/GB2005/005056, dated Jul. 3, 2007.

International Search Report for International Application No. PCT/GB2005/005056, dated Mar. 31, 2006.

Written Opinion for International Application No. PCT/GB2005/005056, dated Jul. 3, 2007.

Search Report for Application No. GB0428445.1, dated Jun. 16, 2005.

* cited by examiner

"DPF"

Figure 5

"n-bu PFB"

"tbu PFB"

BLUE-SHIFTED TRIARYLAMINE POLYMER

BACKGROUND OF THE INVENTION

1. Field of the Invention

The invention is concerned with a semiconductive conjugated polymer, and uses thereof. Further, the invention is concerned with a monomer for making the semiconductive conjugated polymer and an optical device containing the semiconductive conjugated polymer.

2. Related Technology

Optical devices include organic light-emitting diodes (OLEDs), photodetectors, and photovoltaics (PVs). Such devices typically comprise one or more semiconductive polymer layers located between electrodes. Semiconductive polymers are characterised by partial or substantial pi-conjugation in the backbone or side chains.

Semiconductive polymers are now frequently used in a number of optical devices such as in light emitting diodes (LED) as disclosed in WO 90/13148; photovoltaic devices as disclosed in WO 96/16449; and photodetectors as disclosed in U.S. Pat. No. 5,523,555.

For organic semiconductors, important characteristics are the binding energies, measured with respect to the vacuum level of the electronic energy levels, particularly the "highest occupied molecular orbital" (HOMO) and the "lowest unoccupied molecular orbital" (LUMO) level. These can be estimated from measurements of photoemission and particularly measurements of the electrochemical potentials for oxidation and reduction. It is well understood in this field that such energies are affected by a number of factors, such as the local environment near an interface, and the point on the curve (peak) from which the value is determined. Accordingly, the use of such values is indicative rather than quantitative.

The optical and electronic properties of an organic semiconductor are highly dependent on the energy of the aforementioned HOMO and LUMO levels. Furthermore, these energy levels are highly dependent on the chemical structure of the organic semiconductor. By selecting suitable materials, or combinations of materials, device performance can be improved.

A typical LED comprises a substrate, on which is supported an anode, a cathode, and an organic electroluminescent layer, the organic electroluminescent layer being located between the anode and cathode and comprising at least one luminescent material. The luminescent material often is an electroluminescent material and further, often is a polymer. In operation, holes are injected into the device through the anode and electrons are injected into the device through the cathode. The holes and electrons combine in the organic electroluminescent layer to form an exciton, which then undergoes radiative decay to give light. Other layers may be present in the LED. For example a layer of organic hole injection material, such as poly(ethylene dioxy thiophene)/polystyrene sulfonate (PEDT/PSS), may be provided between the anode and the organic electroluminescent layer to assist injection of holes from the anode to the organic electroluminescent layer. A hole transport layer may be provided between the hole injection layer and the organic electroluminescent layer. An electron transport layer may be provided between the cathode and the organic electroluminescent layer.

As described in WO 96/16499, a typical photovoltaic device comprises a photoresponsive zone having first and second major surfaces and first and second electrodes provided on respective ones of the first and second major surfaces of the photoresponsive zone. The photoresponsive zone comprises an electron accepting polymer and an electron donating polymer which may be provided as separate layers or as a blend. Under short-circuit conditions, an internal electric field exists within the photoresponsive zone. The orientation of the internal electric field is such that electrons migrate to and are collected at the contact with the lowest work function, generally an aluminum, magnesium or calcium electrode while holes move towards the electrode with the higher work function, such as an indium tin oxide electrode. Thus, a photocurrent is generated and may be used, for example, to provide electrical power as in the case of a solar cell, for example, or to enable detection of part of a light pattern such as an image for use in an image sensor.

When a polymer is used in an optical device, the polymer preferably is soluble in common organic solvents to facilitate its deposition during device manufacture. One of the key advantages of this solubility is that a polymer layer can be fabricated by solution processing, for example by spin-casting, ink-jet printing, screen-printing, dip-coating etc.

A semiconductive light-emitting polymer is required to transport charge to the emissive unit in the polymer. Typical examples of good charge transport materials are polymers with extended conjugation lengths.

However, increasing the level of conjugation in a semiconductive polymer decreases the band gap of the polymer. This creates a problem for obtaining blue light-emitting polymers having good charge transport properties because blue light-emitting polymer are characterised by a relatively wide band gap. In the prior art therefore, for a blue emitter, the color of the light emitted by a polymer having sufficient charge transport properties often is not as blue as is desirable.

In view of the above, there exists a problem to provide alternative blue light-emitting polymers with good charge transport properties.

Previously, efforts have been made to solve this problem by providing triarylamine-containing semiconductive light-emitting polymers, as discussed below.

Semiconductive triarylamine-containing polymers are known for use in optical devices. A triarylamine typically is incorporated into the polymer backbone through two of its aryl groups, with the third aryl group being pendent from the polymer backbone. U.S. Pat. No. 5,728,801 discloses poly (arylamines), said to be useful as charge transport layers in light emitting devices. Wo99/54385 discloses copolymers comprising a fluorene repeat unit and a triarylamine repeat unit. The copolymers are used as hole transport materials in a device.

WO00/55927 further discloses copolymers containing triarylamine repeat units. WO 00/55927 discloses a blue electroluminescent polymer of formula (a):

wherein w+x+y=1, w< 0.5, 0≦x+y≦0.5 and n< 2. Blue emission in the aforementioned prior art is provided by the "PFB" unit.

WO 02/92723 and WO 02/92724 disclose replacement of some of the F8 repeat units in the polymer illustrated above with 9,9-diarylfluorene repeat units which has surprisingly been found to improve lifetime of the polymer. Likewise, WO2003/095586 and WO 04/084260 disclose optimisation of blue emitting polymers by optimisation of amine content.

In the prior art, substituents on the pendent aryl group in a triarylamine unit are limited to small groups, often incorporated in order to improve solubility.

The invention provides alternative blue light-emitting polymers with good charge transport properties.

Invention involves blue-shifting the light emitted from a triarylamine-containing, blue light-emitting polymer.

According to the first aspect of the invention, there is provided a semiconductive conjugated polymer comprising a first repeat unit comprising general formula I:

I where $Ar_1$, $Ar_3$, and $Ar_5$ are the same or different and each represent an optionally substituted aryl or heteroaryl group; $Ar_2$ and $Ar_4$ are the same or different and each represent a substituted aryl or heteroaryl group; and characterised in that $Ar_2$ and $Ar_4$ sterically interact with one another so as to cause an increase in the bandgap of the polymer.

Where the semiconductive conjugated polymer comprises regions, where each region has a distinct bandgap, the bandgap will be caused to increase in any region comprising a repeat unit of formula I due to steric interaction.

The term "repeat unit" as used herein refers to any recurring structural unit in the polymer. A "repeat unit" may be a monomer residue (i.e. the structural unit incorporated into the polymer from a single monomer), although it is not so limited.

An increased bandgap effectively blue-shifts the fluorescent emission colour of the polymer. Therefore, the present polymer has been found to give good blue emission in combination with good charge transport properties when used in a light emitting device. Blue emission can be characterised by the CIE y-coordinate and a blue-shift in the y-coordinate is observed with the present polymer as compared with the corresponding polymer where $Ar_2$ and $Ar_4$ do not interact sterically with one another.

Also, it is thought that the present polymers also will have a higher T1 energy level than the corresponding polymer where $Ar_2$ and $Ar_4$ do not sterically interact with one another. A high T1 energy level is advantageous for materials to be used as hosts for phosphorescent dopants. The higher T1 level is combined with good charge transport properties, which derive from the conjugated backbone.

Without wishing to be bound by theory, it is thought that the advantageous increase in the bandgap, while maintaining good charge transport properties, results from a twist in the polymer, which is caused by the steric interaction between $Ar_2$ and $Ar_4$. The effect of blue-shifting the color of emission may be observed to varying extents depending on the degree of twisting. In one embodiment of the twisted position, $Ar_2$ and $Ar_4$ will lie on opposite sides of polymer chain. This is shown below for the case where $Ar_1=Ar_2=Ar_3=Ar_4=Ar_5=$phenyl. This twist has not been reported before since generally, in prior art polymers, there is no interaction between the substituents on the pendent phenyl groups.

where X and X' are substituent groups.

The twist and the consequent increase in the bandgap were observed during experiments concerned with improving the lifetime of blue emitting polymers where a change in the optical properties was not intended. The experiments aimed to obtain a shielding effect from side groups on one side of a blue-emitting polymer backbone to avoid aggregation, in the same manner as described in Journal of the American Chemical Society, Vol. 123, Number 29, Jul. 25, 2001, where bulky side groups on poly(fluorene)copolymers were found to lead to an aggregation free solid state spectra. In Journal of the American Chemical Society, Vol. 123, Number 29, Jul. 25, 2001, it is stated that the optical properties of the copolymers are identical to those of high molecular weight polyfluorenes carrying alkyl chains as solubilisers.

Referring to formula I, preferably $Ar_2$ and $Ar_4$ are the same.

In order to achieve the desired steric interaction between $Ar_2$ and $Ar_4$, preferably $Ar_2$ and/or $Ar_4$ has a high molecular weight, such as greater than 200, more preferably greater than 300. However, a high molecular weight is not essential and a steric interaction has been observed by the present inventors where $Ar_2$ and/or $Ar_4$ has a molecular weight of less than 200. In the case of lower molecular weight $Ar_2$ and $Ar_4$, the positioning of the substituents on the aryl or heteroaryl group comprised in $Ar_2$ or $Ar_4$ plays a more important role in enabling a steric interaction between $Ar_2$ and $Ar_4$.

It is preferred that the present polymer is solution processable. To this end, $Ar_2$ and/or $Ar_4$ may have a substituent group comprising a solubilizing group.

Branching groups are desirable for obtaining a steric interaction between $Ar_2$ and $Ar_4$. However, bulky linear groups of sufficient length also can achieve a steric interaction.

Preferably, $Ar_2$ and/or $Ar_4$ contains a branching group. By branching group is meant any group being linked to three or more adjacent groups. Branching groups are desirable since they impart some degree of rigidity to $Ar_2$ and/or $Ar_4$. This is advantageous for encouraging steric interaction between $Ar_2$ and $Ar_4$, which increases the bandgap. It will be appreciated that linear groups will have greater flexibility than branched groups and thus will have a greater capability to bend away from each other without the polymer having to twist, thereby reducing the desired steric interaction.

A preferred branching group consists of an aryl or heteroaryl group, in particular a phenyl group. However, the branching group is not so limited and the branching group may consist of a multivalent atom (for example an sp2 or sp3 hybridized carbon atom). A preferred branching phenyl group is shown below:

Preferably, $Ar_2$ and/or $Ar_4$ comprises a group having formula II

II where X represents a substituent group. Preferably, X comprises a branching group. As mentioned above, the position of X on Ar can be important for achieving a steric interaction between $Ar_2$ and $Ar_4$.

In a first embodiment, preferably, Ar represents a 6-membered aryl or heteroaryl group (shown below), for example a phenyl group. Where Ar represents a 6-membered aryl or heteroaryl group, for ease of synthesis X may be located at the para position, although it may be located at the ortho/meta position. In some cases it may be preferable for X not to be located at the para position when Ar represents a phenyl group, particularly where X represents —$N(Ar)_2$. Positioning X at the meta position may be important for achieving a steric interaction between $Ar_2$ and $Ar_4$.

Preferably, one of $Ar_2$ and $Ar_4$ represents a group having formula II, where Ar represents a 6-membered aryl or heteroaryl group where X is located at the meta position. More preferably, both of $Ar_2$ and $Ar_4$ each independently represents a group having formula II, where Ar represents a 6-membered aryl or heteroaryl group where X is located at the meta position. When X is meta linked it is non-conjugated to the polymer backbone and therefore less likely to contribute to the electronic properties of the polymer.

Where, both of $Ar_2$ and $Ar_4$ each independently represents a group having formula II, where Ar represents a 6-membered aryl or heteroaryl group where X is located at the meta position, in order to maximise steric interaction the meta positions may be chosen so that the X groups point towards each other (i.e. one X on the 3 position and the other X on the 5 position):

In the first embodiment, X may comprise a branched alkyl group. In particular X may consist of a branched alkyl group. X may consist of a branched C4 to C10 alkyl group, although larger alkyl groups may be preferred. Where both $Ar_2$ and $Ar_4$ represent a group having formula II where Ar represents a 6-membered aryl or heteroaryl group and X is in the meta position, a blue-shift has been observed even where X=t-bu.

In the first embodiment, preferably X comprises a group having formula III:

III where $Ar_6$ represents an aryl or heteroaryl group and $Ar_7$ and $Ar_8$ are the same or different and each represents a substituent group. The nature and position of $Ar_7$ and $Ar_8$ preferably are selected so that they have no electronic interaction with the remainder of the polymer, in other words so that they do not contribute to the electronic properties of the polymer as a whole. In order to contribute to the electronic properties of the polymer, a group would have to have either a higher occupied molecular orbital energy level or a lower unoccupied molecular orbital energy level than the groups in the backbone of the polymer.

Groups that are unlikely to contribute to the electronic properties of the polymer as a whole include phenyl and alkyl groups.

In formula III, $Ar_6$ is a branching group.

$Ar_7$ and/or $Ar_8$ may comprise a branching group.

Preferably, $Ar_6$ represents an optionally substituted, although preferably unsubstituted, aryl or heteroaryl ring, more preferably a 6-membered ring, most preferably a phenyl group. In this case, $Ar_7$ and/or $Ar_8$ preferably are located at the meta positions on $Ar_6$.

$Ar_7$ and/or $Ar_8$ may represent a branched alkyl group.

Preferably, $Ar_7$ and/or $Ar_8$ represents a group comprising an optionally substituted aryl or heteroaryl group.

An example of a group having general formula III is shown below:

Therefore, $Ar_2$ and/or $Ar_4$ will comprise:

Examples of substituents on the aryl or heteroaryl group comprised in $Ar_7$ and/or $Ar_8$ include:
1) solubilizing groups such as a branched, linear or cyclic C1-C20 alkyl group; a branched, linear or cyclic C1-C20 alkoxy group; a perfluoroalkyl group; a thioalkyl group; an aryl group; an alkylaryl group; an alkoxyaryl group; a heteroaryl group, or a heteroarylalkyl group. Optionally substituted $C_4$-$C_{20}$ alkyl groups and aryl groups are preferred. C1 to C10 alkyl groups are most preferred;
2) electron withdrawing groups such as fluorine, nitro or cyano; and
3) substituents for increasing glass transition temperature (Tg) of the polymer.

Solubilising groups as described above are most preferred.

In a second embodiment, preferably, $Ar_2$ and/or $Ar_4$ comprises a group having formula IV:

where Ar represents an aryl or heteroaryl group and X and X' are the same or different and each represents a substituent group. The nature and position of X and X' should be selected so that they have no electronic interaction with the remainder of the polymer, in other words so that they do not contribute to the electronic properties of the polymer as a whole. In formula IV, Ar is a branching group.

In formula IV, X and/or X' may comprise a branching group.

In formula IV, preferably, Ar represents an optionally substituted, although preferably unsubstituted, aryl or heteroaryl ring, more preferably a 6-membered ring, most preferably a phenyl group. Where Ar represents a 6-membered ring, X and X' preferably are located at the meta positions. When X and X' are meta linked, they are non-conjugated to the polymer backbone and therefore less likely to contribute to the electronic properties of the polymer.

In formula IV, preferably, X and/or X' represents a group comprising an optionally substituted aryl or heteroaryl group. A mono or disubstituted aryl or heteroaryl group is preferred. More preferably, X and/or X' represents a group comprising an optionally substituted phenyl group.

In the second embodiment, preferably, $Ar_2$ and/or $Ar_4$ comprises a group having formula V:

where R and R' represent substituent groups.

Examples of substituents R and R' in formula V include:
1) solubilizing groups such as a branched, linear or cyclic C1-C20 alkyl group; a branched, linear or cyclic C1-C20 alkoxy group; a perfluoroalkyl group; a thioalkyl group; an aryl group; an alkylaryl group; an alkoxyaryl group; a heteroaryl group, or a heteroarylalkyl group. Optionally substituted C4-C20 alkyl groups and aryl groups are preferred. C1 to C10 alkyl groups are most preferred.
2) electron withdrawing groups such as fluorine, nitro or cyano; and
3) substituents for increasing glass transition temperature (Tg) of the polymer.

Solubilizing groups as described above are most preferred.

Preferably, the angle between the planes of $Ar_1$ and $Ar_3$ is greater than 58°, more preferably greater than 60°, most preferably, greater than 63°.

Preferably, the angle between the planes of $Ar_3$ and $Ar_5$ is greater than 58°, more preferably greater than 60°, most preferably, greater than 63°.

Preferably, $Ar_1$ and/or $Ar_3$ and/or and $Ar_5$ represents an optionally substituted, although preferably unsubstituted, aryl or heteroaryl ring, more preferably a 6-membered ring, most preferably a phenyl group.

$Ar_1$ and/or $Ar_3$ and/or and $Ar_5$ may comprise —($Ar_9$-$Ar_{10}$)— where $Ar_9$ and $Ar_{10}$ are the same or different and each represent an optionally substituted aryl or heteroaryl group. Preferably $Ar_3$ comprises —($Ar_9$-$Ar_{10}$)— as shown in formula VI:

VI

Preferably, $Ar_3$ represents a phenyl group or a para-linked diphenyl group as shown below:

VII

VIII

Most preferably, $Ar_3$ represents a phenyl group.

Preferably the two nitrogen atoms on either side of $Ar_3$ are directly bonded to the same aryl or heteroaryl ring comprised in $Ar_3$.

The repeat unit of formula I may comprise a first repeat unit having general formula IX:

IX where $Ar_{11}$ and $Ar_{12}$ each independently represent an optionally substituted aryl or heteroaryl group and $Ar_1$, $Ar_2$, $Ar_3$, $Ar_4$ and $Ar_5$ are as defined anywhere above. According to the invention $Ar_4$ and $Ar_{12}$ may sterically interact with each other to further increase the band gap and therefore to further blue-shift the emission colour.

Preferred $Ar_{12}$ groups are as discussed above in relation to $Ar_2$ and $Ar_4$.

Preferred $Ar_{11}$ groups are as discussed above in relation to $Ar_1$, $Ar_3$, and $Ar_5$.

The repeat unit of formula I may comprise a first repeat unit having general formula X:

X where $Ar_{13}$ and $Ar_{14}$ each independently represent an optionally substituted aryl or heteroaryl group and $Ar_1$, $Ar_2$, $Ar_3$, $Ar_4$, $Ar_5$, $Ar_{11}$ and $Ar_{12}$ are as defined anywhere above. According to the invention $Ar_{12}$ and $Ar_{13}$ may sterically interact with each other to further increase the band gap and therefore to further blue-shift the emission colour.

Preferred $Ar_{13}$ groups are as discussed above in relation to $Ar_2$ and $Ar_4$.

Preferred $Ar_{14}$ groups are as discussed above in relation to $Ar_1$, $Ar_3$, and $Ar_5$.

The conjugated polymer may be at least one of an emissive polymer and a hole transporting polymer. Optionally, the conjugated polymer is a copolymer comprising two or more different repeat units. The conjugated polymer may comprise at least two of a hole transporting repeat unit, an electron transporting repeat unit and an emissive repeat unit.

Preferably, the backbone of the conjugated polymer consists of aryl and/or heteroaryl groups, such as those described herein.

Preferably, the polymer further contains a second repeat unit, the second repeat unit comprising an aryl or heteroaryl group. The second repeat unit is different from the first repeat unit. Preferably, the second repeat unit comprises an aryl or heteroaryl group selected from the group consisting of carbazole; 2,7-linked 9,9 disubstituted fluorene; spirofluorene; indenofluorene; p-linked dialkyl phenylene; p-linked disubstituted phenylene; phenylene vinylene; 2,5-linked benzothiadiazole; 2,5-linked substituted benzothiadiazole; 2,5-linked disubstituted benzothiadiazole; 2,5-linked substituted or unsubstituted thiophene; or a triarylamine. The choice of the second repeat unit will depend on the use to which the polymer is to be put.

The polymer may further contain a third repeat unit, the third repeat unit comprising an aryl or heteroaryl group. The third repeat unit is different from the first and the second repeat units. Preferred third repeat units are as discussed above in relation to the second repeat unit.

The second repeat unit preferably comprises a 1,4-phenylene repeat unit as disclosed in J. Appl. Phys. 1996, 79, 934; a fluorene repeat unit as disclosed in EP 0842208; a indenofluorene repeat unit as disclosed in, for example, Macromolecules 2000, 33(6), 2016-2020; or a spirofluorene repeat unit as disclosed in, for example EP 0707020. Each of these repeat units is optionally substituted. Examples of substituents include solubilising groups such as those defined above in relation to formulae III and V.

Generally, it is preferred that the second repeat unit comprises an optionally substituted, 2,7-linked fluorene, most preferably a repeat unit of formula XI:

XI wherein $R^1$ and $R^2$ are independently selected from hydrogen or optionally substituted alkyl, alkoxy, aryl, arylalkyl, heteroaryl and heteroarylalkyl. More preferably, at least one of $R^1$ and $R^2$ comprises an optionally substituted $C_4$-$C_{20}$ alkyl or aryl group. Preferably, $R^1$ and/or $R^2$ comprises an optionally substituted phenyl group.

The present polymer may provide one or more of the functions of hole transport, electron blocking and emission depending on which layer of the device it is used in, the nature of co-repeat units with the first repeat unit, and what other polymers or small molecules, if any, are blended with the present polymer.

The present polymer may be a copolymer comprising two, three or more different repeat units. Preferred copolymers have two or three different repeat units. Such copolymers may be made from two or three different monomers, respectively, although the invention is not so limited.

Preferably, the copolymer contains up to 20 mol % of a repeat unit of formula I, more preferably up to 10 mol %, still more preferably about 5 mol %.

A copolymer comprising a first repeat unit of formula I and a second phenylene, fluorene, indenofluorene, or spirofluorene repeat unit may be utilised to provide hole transport and/or emission. A third repeat unit may be present. Particularly preferred hole transporting polymers of this type are AB copolymers of the first repeat unit and the second repeat unit. Particularly preferred hole transporting polymers of this type are copolymers of the first repeat unit and a 9,9 disubstituted fluorene such as 9,9 dialkyl fluorene.

A copolymer comprising a first repeat unit of formula I and a second repeat unit, which does not comprise a phenylene, fluorene, indenofluorene, or spirofluorene group, may be utilised as an electron blocking material.

Electroluminescent copolymers may comprise an electroluminescent region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality.

The different regions within such a polymer may be provided along the polymer backbone, as per U.S. Pat. No. 6,353,083, or as groups pendent from the polymer backbone as per WO 01/62869.

A polymer according to the first aspect may be used as a host for a phosphorescent dopant in an optical device.

A typical phosphorescent dopant comprises a metal complex.

Preferred metal complexes comprise optionally substituted complexes of formula (XII):

$$ML^1{}_q L^2{}_r L^3{}_s \quad \text{XII}$$

wherein M is a metal; each of $L^1$, $L^2$ and $L^3$ is a coordinating group; q is an integer; r and s are each independently 0 or an integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet states (phosphorescence). Suitable heavy metals M include:
lanthanide metals such as cerium, samarium, europium, terbium, dysprosium, thulium, erbium and neodymium; and
d-block metals, in particular those in rows 2 and 3 i.e. elements 39 to 48 and 72 to 80, in particular ruthenium, rhodium, palladium, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals form complexes with carbon or nitrogen donors such as porphyrin or bidentate ligands of formula (XIII):

XIII wherein Ar' and Ar''' may be the same or different and are independently selected from optionally substituted aryl or heteroaryl; $X^1$ and $Y^1$ may be the same or different and are independently selected from carbon or nitrogen; and Ar' and Ar''' may be fused together. Ligands wherein $X^1$ is carbon and $Y^1$ is nitrogen are particularly preferred.

Examples of bidentate ligands are illustrated below:

Each of Ar'' and Ar''' may carry one or more substituents. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalize the ligand for attachment of further groups as disclosed in WO 02/68435 and EP 1245659; and dendrons which may be used to obtain or enhance solution processability of the metal complex as disclosed in WO 02/66552.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission colour is determined by the choice of ligand as well as the metal.

The present polymer, when used as a host material, may be combined with a metal complex in the form of a physical blend. Alternatively, the metal complex may be chemically bound to the host material for example as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

A polymer according to the first aspect also may be used to transport charge in an optical device. Further, a polymer according to the first aspect may be used to emit light in an optical device. Typically, a polymer according to the first aspect is a blue electroluminescent material. By "blue electroluminescent material" is meant an organic material that by electroluminescence is capable of emitting blue light. By "blue light" is meant radiation having a wavelength in the range of 400-500 nm, more preferably 430-500 nm, still more preferably 430-480 nm.

A second aspect of the invention provides an optical device containing the polymer according to first the aspect of the invention. Preferably, the optical device comprises an electroluminescent device. However, the present polymer also may be used in the photoresponsive zone of a photovoltaic device, for example.

The optical device according to the second aspect comprises an anode; a cathode; and a layer located between the anode and the cathode comprising a polymer as defined in relation to the first aspect of the invention. Typically, either the anode or the cathode will be supported on a substrate.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

In a practical device, at least one of the electrodes is semitransparent in order that light may be absorbed (in the case of a photoresponsive device) or emitted (in the case of an OLED). Where the anode is transparent, it typically comprises indium tin oxide. Examples of transparent cathodes are disclosed in, for example, GB 2348316.

Figure 1:
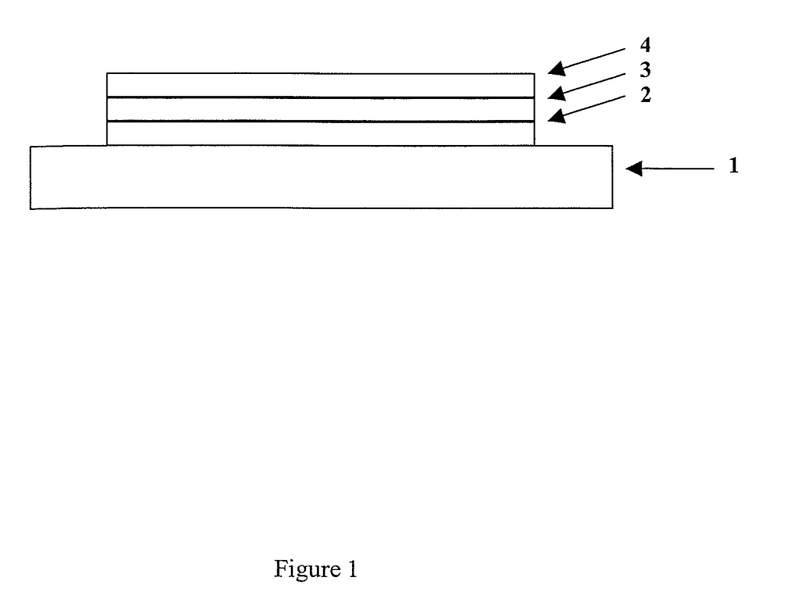
FIG. 1 shows one example of the architecture of an electroluminescent device as defined in relation to the second aspect of the invention.

With reference to FIG. 1, the architecture of an electroluminescent device according to the invention comprises a transparent glass or plastic substrate 1, an anode 2 of indium tin oxide and a cathode 4. An electroluminescent layer 3 is provided between the anode 2 and the cathode 4.

The electroluminescent layer can itself comprise a laminate, effectively made up of sub-layers.

Further layers may be located between the anode 2 and the cathode 3, such as charge transporting, charge injecting or charge blocking layers.

In particular, it is desirable to provide a conductive hole injection layer formed of a doped organic material located between the anode 2 and the electroluminescent layer 3 to assist hole injection from the anode into the layer or layers of semiconducting polymer. Examples of doped organic hole injection materials include poly(ethylene dioxythiophene) (PEDT), in particular PEDT doped with polystyrene sulfonate (PSS) as disclosed in EP 0901176 and EP 0947123, or polyaniline as disclosed in U.S. Pat. No. 5,723,873 and U.S. Pat. No. 5,798,170.

If present, a hole transporting layer located between the anode 2 and the electroluminescent layer 3 preferably has a HOMO level of less than or equal to 5.5 eV, more preferably around 4.8-5.5 eV.

If present, an electron transporting layer located between the electroluminescent layer 3 and the cathode 4 preferably has a LUMO level of around 3-3.5 eV.

A hole transport layer located between the anode and the electroluminescent layer may comprise the present polymer. In this case the present polymer will be used to transport holes from the anode to the electroluminescent layer and the electroluminescent layer will comprise a separate electroluminescent material.

The electroluminescent layer may comprise the present polymer. In this case the present polymer will be used to transport charge and/or to emit light.

Where the present polymer is used to transport charge, the present polymer may be blended with an electroluminescent material or covalently bound to an electroluminescent material.

Suitable electroluminescent polymers for use in layer 3 include poly(arylene vinylenes) such as poly(p-phenylene vinylenes) and polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein.

Where the present polymer is used to emit light, the electroluminescent layer 3 may consist of the present electroluminescent polymer alone or may comprise the electroluminescent polymer in combination with one or more further materials. In particular, the electroluminescent polymer may be blended with hole and/or electron transporting materials as disclosed in, for example, WO 99/48160. Alternatively, the electroluminescent polymer may be covalently bound to a charge transporting material.

The cathode 4 is selected from materials that have a work-function allowing injection of electrons into the electroluminescent layer. Other factors influence the selection of the cathode such as the possibility of adverse interactions between the cathode and the electroluminescent material. The cathode may consist of a single material such as a layer of aluminum. Alternatively, it may comprise a plurality of metals, for example a bilayer of calcium and aluminum as disclosed in WO 98/10621, elemental barium disclosed in WO 98/57381, Appl. Phys. Lett. 2002, 81(4), 634 and WO 02/84759 or a thin layer of dielectric material to assist electron injection, for example lithium fluoride disclosed in WO 00/48258 or barium fluoride, disclosed in Appl. Phys. Lett. 2001, 79(5), 2001. In order to provide efficient injection of electrons into the device, the cathode preferably has a work-function of less than 3.5 eV, more preferably less than 3.2 eV, most preferably less than 3 eV.

The embodiment of FIG. 1 illustrates a device wherein the device is formed by firstly forming an anode on a substrate followed by deposition of an electroluminescent layer and a cathode, however it will be appreciated that the device of the invention could also be formed by firstly forming a cathode on a substrate followed by deposition of an electroluminescent layer and an anode.

A third aspect of the invention provides a monomer for making a polymer as defined in relation to the third aspect, having a formula XIV:

XIV where $Ar_1$, $Ar_2$, $Ar_3$, $Ar_4$, $Ar_5$, $Ar_{11}$ and $Ar_{12}$ are as defined in relation to the first aspect; n=0, 1, or 2; and Y and Y' each represent a reactive group suitable for participating in a polymerization reaction.

Preferred reactive groups Y and Y' are as described below in relation to the fourth aspect of the invention.

The fourth aspect of the invention provides a method of making a polymer as defined in relation to the first aspect, said method comprising the step of polymerising a plurality of first monomers, each first monomer being a monomer as defined in the third aspect.

Preferably, the plurality of first monomers is polymerized together with a plurality of second monomers, where the second monomer comprises an aryl or heteroaryl group and is different to the first monomer. Preferably, the plurality of first monomers and the plurality of second monomers are polymerized together with a plurality of third monomers, where the third monomer comprises an aryl or heteroaryl group and is different to the first and second monomers.

Repeat units and end groups comprising aryl groups as illustrated herein may be derived from a monomer carrying a suitable leaving group.

Preferred methods for preparation of these polymers are metal mediated coupling reactions, forming a direct bond between two aryl/heteroaryl groups. Examples of such coupling reactions are Suzuki polymerization as described in, for example, WO 00/53656 and Yamamoto polymerization as described in, for example, T. Yamamoto, "Electrically Conducting And Thermally Stable π-Conjugated Poly(arylene)s Prepared by Organometallic Processes", Progress in Polymer Science 1993, 17, 1153-1205. These polymerization techniques both operate via a "metal insertion" wherein the metal atom of a metal complex catalyst is inserted between an aryl group and a leaving group of a monomer. In the case of Yamamoto polymerization, a nickel complex catalyst is used.

For example, in the synthesis of a linear polymer by Yamamoto polymerization, a monomer having two reactive halogen groups is used.

In overview, Suzuki polymerization involves polymerizing monomers in the presence of a catalyst and a base. The reaction involves a reactive group on one monomer and a reactive group on another monomer. Palladium is a preferred catalyst. Organic bases are preferred.

One of the reactive groups involved in the Suzuki coupling reaction will be a boron derivative group selected from boronic acid, boronic acid ester (preferably $C_1$-$C_6$)), and borane (preferably $C_1$-$C_6$). Boronic acid is preferred.

The other reactive group involved in the Suzuki coupling reaction typically will be a halide or sulfonate. A preferred halide group is bromide. Examples of suitable sulfonate reactive groups include triflate, mesylate, phenyl sulfonate, and tosylate.

Each monomer will have at least two reactive groups. Suzuki polymerisation may be used to prepare regioregular, block and random copolymers. In particular, homopolymers or random copolymers may be prepared when each monomer has one reactive halide or sulfonate group and one reactive boron derivative group. Alternatively, block or regioregular, in particular AB, copolymers may be prepared when both reactive groups of a first monomer are boron derivative groups and both reactive groups of a second monomer are halide or sulphonate.

The nature of the reactive end groups on the charge transport polymers and the host polymers can be selected so that the polymers are combined together in the phosphorescent material to form charge transport regions and host regions in the desired order. Preferably, the phosphorescent material comprises alternating charge transport regions and host regions.

Suzuki polymerization may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

A fifth aspect of the invention provides a method of making an optical device as defined in relation to the second aspect of the present invention. The method according to the fifth aspect includes the step of depositing a layer comprising the polymer as defined in relation to the first aspect.

Preferably, the layer comprising the polymer as defined in relation to the first aspect is deposited from solution by a solution processing technique. Suitable solvents for polyarylenes include mono- or poly-alkylbenzenes such as toluene and xylene. Particularly preferred solution deposition techniques are spin-coating and inkjet printing.

Spin-coating is particularly suitable for electroluminescent devices wherein patterning of the electroluminescent material is unnecessary—for example for lighting applications or simple monochrome segmented displays.

Inkjet printing is particularly suitable for high information content displays, in particular full colour displays. Inkjet printing of organic OLEDs is described in, for example, EP 0880303.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

DETAILED DESCRIPTION

Examples

The present invention will now be described in more detail with reference to the attached drawings, in which.

Example 1

Preparation of Monomer (2)

Figure 2:
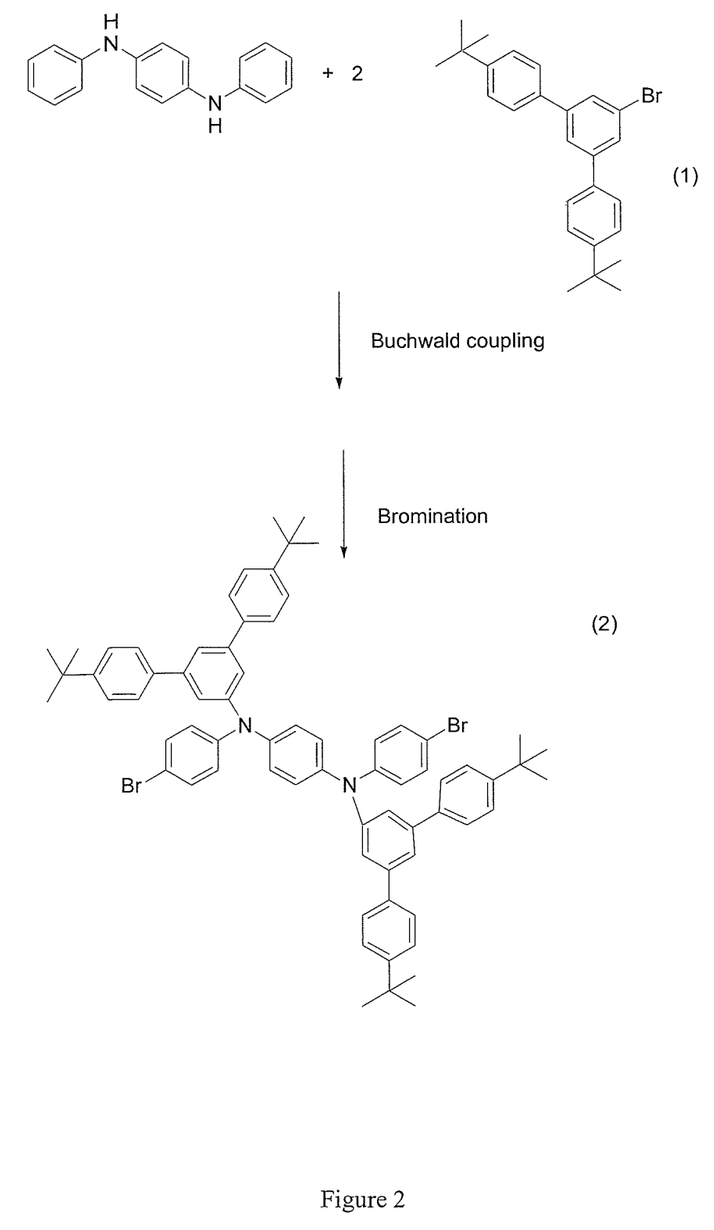
FIG. 2 shows schematically the preparation of monomer (2)

3,3-bis(t-butylphenyl)-1-bromo-benzene (1) was formed from a mixture of 4-tert-butylphenyl boronic acid (2.1 eq), 1,3,5-tribromobenzene (1 eq.), tetrakis(triphenylphosphine) palladium (0) catalyst, 2 M $Na_2CO_3$(aq) and a mixed solvent of degassed ethanol and toluene which was heated to reflux under argon. Monomer (2) was prepared by reacting 3,3-bis (t-butylphenyl)-1-bromo-benzene (1) with N,N'-diphenyl-1, 4-phenylenediamine using Buchwald coupling. The product was brominated to give the aromatic amine monomer (2) as shown in FIG. 2.

Example 2

Preparation of Monomer 1

-continued

Procedure

To a 2 L 3 neck round bottom flask equipped with thermometer, dropping funnel, magnetic stirrer bar, condenser and nitrogen inlet was added magnesium powder (22.44 g). This was then stirred under nitrogen for 1 hour. To the magnesium powder was added anhydrous THF (400 ml) and a few crystals of iodine. A solution of 4-bromo-t-butylbenzene (200 g) in THF (450 ml) was cannulated into the dropping funnel. A small amount (approx. 10 ml) was added to the magnesium/ THF slurry which was heated with stirring. Small amounts more of the 4-bromo-t-butylbenzene solution were added and the reaction mixture maintained at reflux. The rest of the reagent was added dropwise maintaining reflux. The reaction mixture was left at reflux overnight, then cooled to 22° C. The 2,4,6 tribromo iodobenzene (123.4 g) was dissolved in anhydrous THF (400 ml) and added dropwise with stirring to the reaction mixture at 22° C. After addition the reaction mixture was heated to reflux for 3 h, then at 75° C. for 72 h. Poured reaction mixture into 1 L ice water containing 100 ml conc. HCl. Stirred for 60 min. The organic layer was separated and the aqueous layer washed twice with toluene. Dried over magnesium sulphate and concentrated to give an oil. The oil was passed through a silicon column eluted with hexane to give a white solid (79 g, 67% yield)

Example 3

Preparation of Monomer 2 (Unbrominated)

Procedure

To a 3 neck 250 ml round bottom flask equipped with overhead stirrer and condenser with nitrogen inlet was added palladium acetate (60 mg) and tris(o-tolyl)phosphine (180 mg) in 100 ml of toluene, stirred for 15 min. The N,N'-diphenyl-1,4-phenylene diamine (3.47 g), monomer 1 (12.32 g) and sodium t-butoxide (3.84 g) were added in a small amount of toluene (total volume 150 ml). Left at reflux for 24 h, then the addition of catalyst and ligand was repeated and reflux continued for a further 24 h. Poured reaction mixture into water (500 ml). Separated the organic phase and washed the aqueous phase with toluene. Combined organic phases and dried over magnesium sulphate. Filtered and concentrated to dryness to give brown oil. Passed through silica column and eluted with hexane, re-crystallised from hexane/toluene to give white solid (5.52 g, 44% yield)

Example 4

Preparation of Monomer 2

Procedure

To a 250 ml round bottom three neck flask equipped with condenser, nitrogen inlet, and magnetic stirrer was added the amine monomer (5.405 g) and dichloromethane (140 ml). The reaction mixture was stirred to give a solution and cooled to 5° C. in an ice bath. N-Bromosuccinimide (2.15 g) was added and the reaction mixture was allowed to warm to 22° C. over 3 h with stirring, the reaction mixture was washed with water (200 ml), this was repeated twice more. The organic function was dried over magnesium sulphate, filtered and concentrated to dryness. The product was triturated with hexane and re-crystallised from hexane/toluene to give a white solid (3.63 g, 58% yield).

Example 5

Preparation of Monomer (4)

Figure 3:
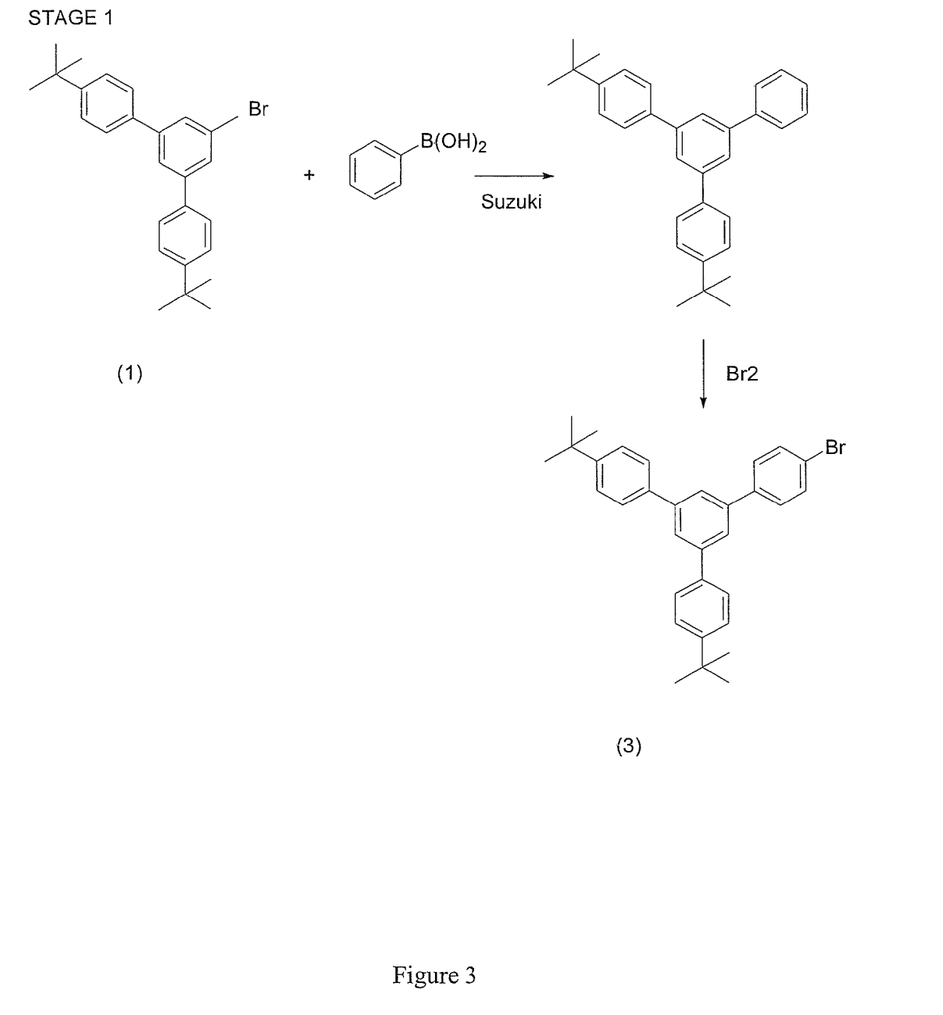
FIGS. 3 and 4 show schematically the preparation of monomer (4) via a two stage process.
Figure 4:
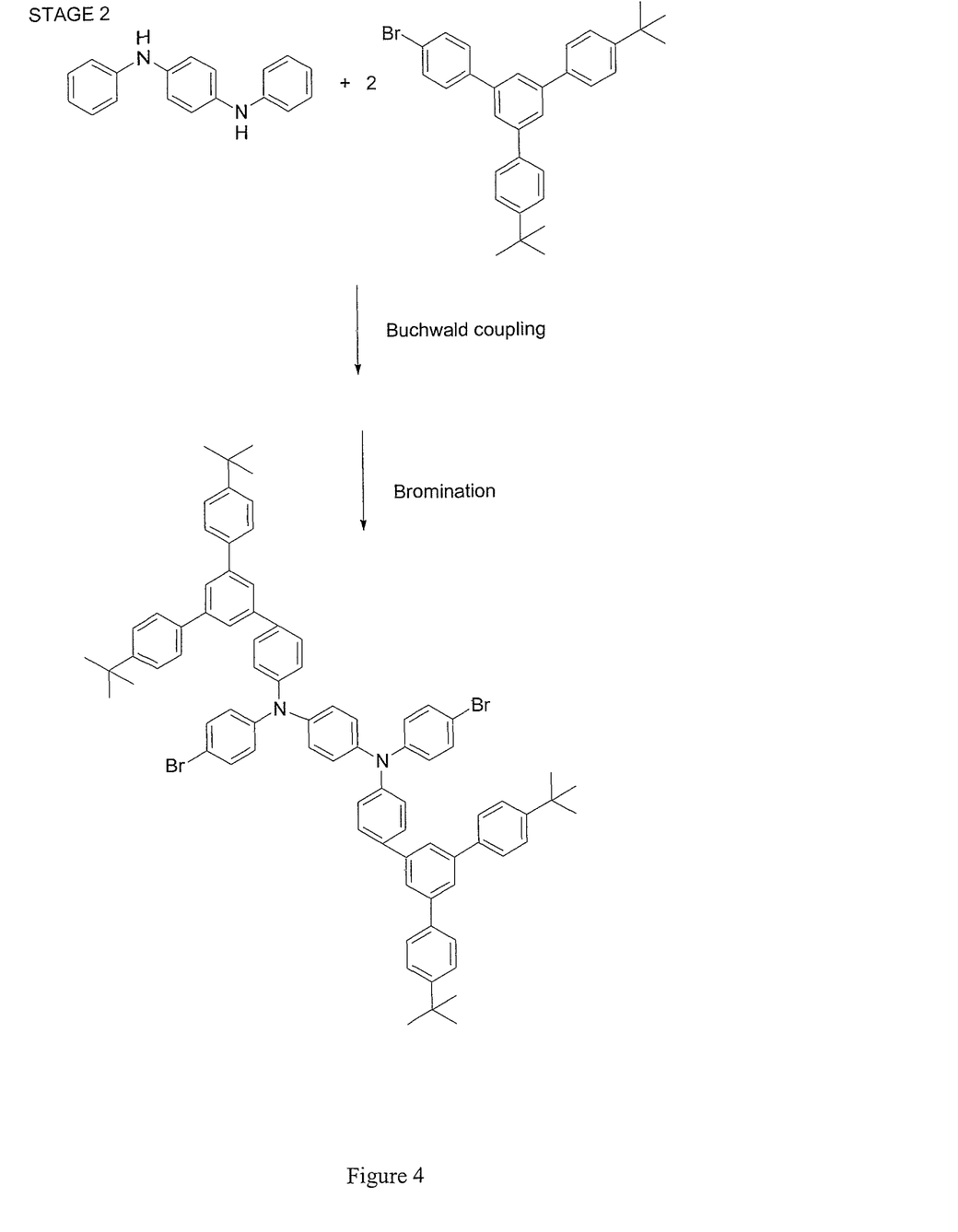
Figure 5:
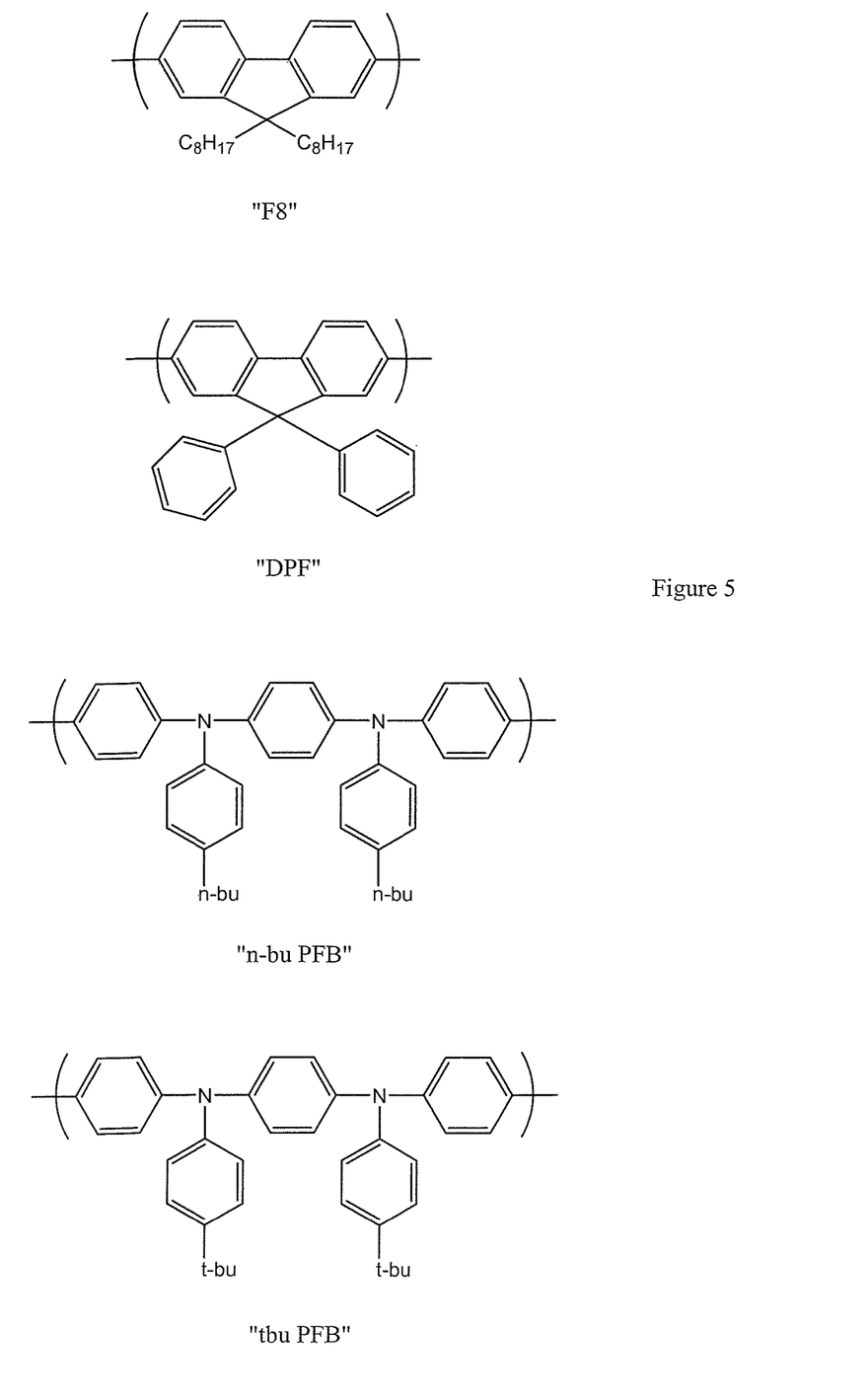
FIG. 5 shows the structure of F8, DPF, n-bu PFB, and t-bu PFB repeat units.

The 3,3-bis(t-butylphenyl)-1-bromo-benzene (1) prepared according to the method in Example 1 was reacted with phenyl boronic acid and the resulting product brominated to give (3) as shown in FIG. 3. The product 3 is then reacted with N,N'-diphenyl-1,4-phenylenediamine using Buchwald coupling and the product brominated to give the aromatic amine monomer (4) as shown in FIG. 4.

Example 6

Preparation of Polymer (1)

Using Suzuki polymerization, monomer 2 was incorporated into the following polymer (1): 65% F8, 30% DPF, 5% repeat unit from monomer 2.

To a 3 neck 250 ml round bottom flask equipped with overhead stirrer, condenser and nitrogen inlet was added F8 diester (2.3866 g), F8 dibromide (0.7404 g), monomer 2 dibromide (0.4946 g) and DPF dibromide (1.2857 g) in toluene (50 ml). The resulting mixture was stirred for 5 minutes, then degassed by bubbling nitrogen through the solution for a period of 10 minutes. The reaction mixture was then heated to 65° C. with stirring until a complete solution was obtained. The catalyst, bis-(triphenylphosphine) palladium dichloride (9 mg) was added to the reaction mixture with a small amount of toluene then tetraethyl ammonium hydroxide (15 ml of 20% aqueous solution) added and the reaction mixture brought to reflux for 24 h, the polymer was end capped with bromobenzene (0.5 ml) and phenyl boronic acid (0.5 g) each at reflux for 60 min.

The polymer was worked up in accordance with the method described in WO 00/53656.

Materials Science Data

HOMO levels were measured by cyclic voltametry. The results show that the repeat unit from monomer 4 has a HOMO level slightly deeper than PFB (5.1 eV, as compared with 4.9 eV, in the polymers tested).

Example 7

LED

Poly(ethylene dioxythiophene)/poly(styrene sulfonate) (PEDT/PSS), available from H C Starck of Leverkusen, Germany as Baytron P® was deposited over an indium tin oxide anode supported on a glass substrate (available from Applied Films, Colorado, USA) by spin coating. A hole transporting layer of F8-TFB (shown below) is deposited over the PEDT/PSS layer by spin coating from xylene solution to a thickness of about 10 nm and heated at 180° C. for 1 hour. Polymer 1 prepared in Example 6 is deposited over the layer of F8-TFB by spin-coating from xylene solution to a thickness of around 65 nm. A Ba/Al cathode is formed over polymer 1 by evaporating a first layer of barium to a thickness of up to about 10 nm and a second layer of aluminum barium to a thickness of about 100 nm over the semiconducting polymer. Finally, the device is sealed using a metal enclosure containing a getter that is placed over the device and glued onto the substrate in order to form an airtight seal.

Results summary:

| polymer | CIE-y |
|---|---|
| Comparison (a) | 0.232 |
| Comparison (b) | 0.233 |
| Polymer (1) | 0.136 |

The results show that the colour of the polymer (1) device emission is much bluer.

Example 8

Results on Bulky PFB (Showing Increased Twist)

(2)

The structure above ("bulky PFB") was modelled using standard modelling software along with tBu PFB where the tBu groups are in the meta positions (nothing on the para position). As a measure of twist in the system, the angle between the planes of phenyl ring 1 and phenyl ring 2 and the angle between the planes of phenyl ring 2 and phenyl ring 3 were compared for the different monomers. The results are shown below:

| Monomer | Angle (1&2) | Angle (2&3) |
|---|---|---|
| Bulky PFB (shown above) | 63.5 | 58.8 |
| tBu (meta) PFB | 63.5 | 58.4 |

Results Show

High twist for both bulky PFB and also tBu PFB where the tBu is in the meta position (NB: tBu in the para position does not give twist)

"Standard modelling software" is as follows:
1) AM1 in Ampac program package Ampac 5.0 User's Manual, C 1994 Semichem, 7128 Summit, Shawnee, Kans. 66216
2) ZINDO from Gaussian software:
Gaussian 98, Revision A.9, M. J. Frisch, G. W. Trucks, H. B. Schlegel, G. E. Scuseria, M. A. Robb, J. R. Cheeseman, V. G. Zakrzewski, J. A. Montgomery, Jr., R. E. Stratmann, J. C. Burant, S. Dapprich, J. M. Millam, A. D. Daniels, K. N. Kudin, M. C. Strain, O. Farkas, J. Tomasi, V. Barone, M. Cossi, R. Cammi, B. Mennucci, C. Pomelli, C. Adamo, S. Clifford, J. Ochterski, G. A. Petersson, P. Y. Ayala, Q. Cui, K. Morokuma, D. K. Malick, A. D. Rabuck, K. Raghavachari, J. B. Foresman, J. Cioslowski, J. V. Ortiz, A. G. Baboul, B. B. Stefanov, G. Liu, A. Liashenko, P. Piskorz, I. Komaromi, R. Gomperts, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, J. L. Andres, C. Gonzalez, M. Head-Gordon, E. S. Replogle, and J. A. Pople, Gaussian, Inc., Pittsburgh Pa., 1998.

The invention claimed is:

1. A semiconductive conjugated polymer comprising a first repeat unit comprising general formula I:

$$\left(Ar_1-N(Ar_2)-Ar_3-N(Ar_4)-Ar_5\right) \quad I$$

wherein $Ar_1$, $Ar_3$, and $Ar_5$ are the same or different and each represents an optionally substituted aryl or heteroaryl group; each of $Ar_2$ and $Ar_4$ comprises a group having formula II:

$$\text{Ar}-X \quad II$$

wherein Ar represents a 6-membered aryl or heteroaryl group; and

X comprises a group having formula III:

$$Ar_6(Ar_7)(Ar_8) \quad III$$

wherein $Ar_6$ represents a 6-membered aryl or heteroaryl group and $Ar_7$ and $Ar_8$ are the same and each represents an aryl or heteroaryl group located at the meta position;

wherein $Ar_2$ and $Ar_4$ sterically interact with one another so as to cause an increase in the bandgap of the polymer relative to a corresponding polymer wherein $Ar_2$ and $Ar_4$ do not sterically interact with one another; and wherein both $Ar_2$ and $Ar_4$ have a molecular weight of greater than 300.

2. A polymer according to claim 1 wherein $Ar_2$ and $Ar_4$ are the same.

3. A polymer according to claim 1, wherein one of $Ar_2$ and $Ar_4$ represents a group having formula II wherein Ar represents a 6-membered aryl or heteroaryl group and wherein X is located at the meta position.

4. A polymer according to claim 3, wherein both of $Ar_2$ and $Ar_4$ each independently represents a group having formula II wherein Ar represents a 6-membered aryl or heteroaryl group and wherein X is located at the meta position.

5. A polymer according to claim 1, wherein $Ar_6$ represents a phenyl group.

6. A polymer according to claim 1, wherein X represents a group comprising an optionally substituted phenyl group.

7. A polymer according to claim 6, wherein $Ar_2$ and/or $Ar_4$ comprises a group having formula V:

$$V$$

wherein R and R' represent substituent groups.

8. A polymer according to claim 1 wherein at least one of $Ar_1$, $Ar_3$, and $Ar_5$ represents an optionally substituted phenyl group.

9. A polymer according to claim 1, wherein the polymer further contains a second repeat unit, the second repeat unit comprising an aryl or heteroaryl group.

10. A polymer according to claim 9, wherein the second repeat unit comprises an aryl or heteroaryl group selected from the group consisting of carbazole; 2,7-linked 9,9 disubstituted fluorene; spirofluorene; indenofluorene; p-linked dialkyl phenylene; p-linked disubstituted phenylene; phenylene vinylene; 2,5-linked benzothiadiazole; 2,5-linked substituted benzothiadiazole; 2,5-linked disubstituted benzothiadiazole; 2,5-linked substituted or unsubstituted thiophene; and triarylamines.

11. A polymer according to claim 10, wherein the second repeat unit comprises a 2,7-linked 9,9 disubstituted fluorene.

12. A polymer according to claim 1 wherein the polymer further contains a third repeat unit, the third repeat unit comprising an aryl or heteroaryl group.

13. An optical device comprising:
   an anode;
   a cathode; and
   a layer located between the anode and the cathode comprising a polymer as defined in claim 1.

14. An electroluminescent device comprising:
   an anode;
   a cathode;
   an electroluminescent layer located between the anode and the cathode; and
   optionally a hole transport layer located between the anode and the electroluminescent layer;
   wherein the electroluminescent layer or the hole transport layer comprises a polymer as defined in claim 1.

15. A method of making a polymer as defined in claim 1, said method comprising the step of polymerizing a plurality of first monomers, each first monomer being a monomer having a formula XIV:

$$XIV$$

where $Ar_1$, $Ar_2$, $Ar_3$, $Ar_4$ and $Ar_5$ are as defined in claim 1; $Ar_{11}$ and $Ar_{12}$ each independently represent an optionally substituted aryl or heteroaryl group; n=0, 1, or 2; and Y and Y' each represent a reactive group suitable for participating in a polymerization reaction.

16. A method according to claim 15, comprising polymerizing the plurality of first monomers together with a plurality of second monomers, where the second monomer comprises an aryl or heteroaryl group and is different from the first monomer.

17. A method according to claim 16, comprising polymerizing the plurality of first monomers and the plurality of second monomers together with a plurality of third monomers, where the third monomer comprises an aryl or heteroaryl group and is different from the first and second monomers.

18. A method according to claim 15, comprising polymerizing the monomers by Suzuki polymerization.

19. A method of making an optical device including the step of depositing a layer comprising a polymer as defined in claim 1.

20. A method according to claim 19, comprising depositing the layer comprising the polymer from solution by a solution processing technique.

21. A method according to claim 20, wherein the solution processing technique comprises inkjet printing.

22. A method according to claim 16, comprising polymerizing the monomers by Suzuki polymerization.

23. A method according to claim 17, comprising polymerizing the monomers by Suzuki polymerization.

* * * * *